(12) United States Patent
Feder et al.

(10) Patent No.: US 6,706,513 B2
(45) Date of Patent: Mar. 16, 2004

(54) ADENOSINE DEAMINASE HOMOLOG

(75) Inventors: John N. Feder, Belle Mead, NJ (US); Chandra S. Ramanathan, Wallingford, CT (US); Gabe Mintier, Hightstown, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 85 days.

(21) Appl. No.: 09/933,386

(22) Filed: Aug. 20, 2001

(65) Prior Publication Data

US 2002/0137061 A1 Sep. 26, 2002

Related U.S. Application Data

(60) Provisional application No. 60/261,778, filed on Jan. 16, 2001, and provisional application No. 60/226,786, filed on Aug. 21, 2000.

(51) Int. Cl.$^7$ ........................... C12N 9/78; C12N 15/55; C12Q 1/68
(52) U.S. Cl. ..................... 435/227; 435/6; 435/320.1; 435/252.3; 536/23.2
(58) Field of Search ............................. 435/227, 320.1, 435/252.3, 6; 536/23.2, 24.91

(56) References Cited

FOREIGN PATENT DOCUMENTS

| WO | WO 01/57182 | 9/2001 |
|----|----|----|
| WO | WO 01/57190 | 9/2001 |
| WO | WO0214483 | 4/2002 |
| WO | WO0226998 | 4/2002 |
| WO | WO0238743 | 5/2002 |
| WO | WO0240715 | 5/2002 |
| WO | WO02074960 | 9/2002 |
| WO | WO02077233 | 10/2002 |

OTHER PUBLICATIONS

Strasburg, R., Accession No. A1420327, Mar. 28, 1999.*
Strasburg, R>, Accession No. A1802332, Dec. 13, 1999.*
Diasm, N,E,, et al. Accession No. BE157237, Jun. 21, 2000.*
Simpson, A.J.G., Accession No. AW371891, Feb. 4, 2000.*
Campbell (1991) Biochemistry, Library of Congress Cat. Card. No. 90–052775.
NCBI Accession No. gi:4557249, Yoneyama, et al., Apr. 3, 2002.
NCBI Accession No. gi:6680636, Van De Wiele, et al., Jun. 19, 2003.
NCBI Accession No. gi:3179945, Robert Strausbert, Ph.D., Jun. 3, 1998.
Bhaumik, et al. (1993) J. of Biological Chemistry, 268(8):5464–5470.
Parkman, et al. (2000) Ann. Rev. Med., 51:33–47.
Richard, et al. (2002) J. of Biological Chemistry, 277(22):19720–19726.
Wiginton, et al. (1986), Biochemistry, 25(25):8234–8244.
Valerio, et al. (1984), Gene, 31:147–153.
Berkvens, et al. (1990), Genomics, 7:486–490.
Valerio, et al. (1985), EMBO Journal, 4:437–443.
Blaese, et al. (1995), Science, 270–475–480.
Yoneyama, et al. (2002) Clinica Chimic Acta, 322:169–173.
Valerio, et al. (1983) Gene, 25:231–240.
Gossage, et al. (1993) 2:1493–1494.
Adrian, et al. (1984) Molecular and Cellular Biology, 4(9):1712–1717.
Bonthron, et al. (1985), J. Clin Invest, 76:894–897.
Wiginton, et al. (1984), Nucleic Acids Research 12:2439–2446.
Orkin, et al. (1985), Molecular and Cellular Biology 5(4):762–767.
Daddona, et al. (1984), J. of Biological Chemistry 259(19:12101–12106.
Parkman, R., et al., (2000) Annual Review Medicine—vol. 51; pp 33–47.
Bhaumik, D., et al., (1993) The Journal of Biological Chemistry—vol. 268, No. 8, Mar.15;pp 5464–5470.
NCBI Entrez Genbank Accession No. gi|4557249, Duyvesteyn, V., et al., Jan. 20, 2001.
NCBI Entrez GenBank Accession No. gi|6680636; Yeung, C. Y., et al. Nov. 1, 2000.
Incyte EST (CloneID: 877185) (no date).
NCBI Entrez GenBank Accesson No.:gi| AA993400;ATCC (CloneID: 3246386) ; Image Clone ID No: 1624586 (Aug. 27, 1998).
EMBL Accession No. AI420327 (XP002204329) (Mar. 3, 2000).
EMBL Accession No. AA044789 (XP002204330) (Mar. 3, 2000.
EMBL Accession No. AC018924 (XP002204331) Jan. 22, 2002.
EMBL Accession No. AAM79306 (XP002204332) (Nov. 6, 2001).
EMBL Accession No. AAM80290 (XP002204333) (Nov. 6, 2001).
EMBL Accession No. AAK52439 (XP002204334) (Nov. 6, 2001.

(List continued on next page.)

Primary Examiner—Charles L. Patterson, Jr.
(74) Attorney, Agent, or Firm—Stephen C. D'Amico

(57) ABSTRACT

This invention provides a novel isolated polynucleotide sequence, called ADARP1 (adenosine deaminase related protein 1), that displays significant homology to the adenosine deaminase (ADA) gene. Also provided is the amino acid sequence of the ADARP1 polypeptide encoded by the polynucleotide of the invention. The RNA for this novel gene is found in variety of tissues, with higher levels observed in the heart, testes, and skeletal muscle compared with others tested. Based on amino acid sequence homology, the ADARP1 protein will likely display the catalytic activity characteristic of ADA. This newly found ADARP1 gene and its encoded product may be useful in the treatment of immunodeficiencies, including severe combined immunodeficiency disease (SCID) and other ADA deficiencies, treatment of male reproductive disorders, testicular disorders and musclo-skeletal disorders.

15 Claims, 5 Drawing Sheets

OTHER PUBLICATIONS

EMBL Accession No. AAM90763 (XP002204335) (Nov. 7, 2001).
EMBL Accession No. AAK63544 (XP002204336) (Nov. 6, 2001).
Katayama et al., Gene (1996), 171:135–136.
EMBL Accession No. P53984 (XP002204337) (Oct. 1, 1996).
Wiginton et al. Biochemistry (1986), 25:8234–8244.
Liu et al., Journal of Biological Chemistry (1997) 272:4419–4428.
Vieira et al., FASEB Journal (1996) 10:A131.
Hoogerbrugge et al., British Medical Bulletin (1995), 51:72–81.
NCBI Accession No. gi:21524612, Conklin et al., Jun. 18, 2002.
NCBI Accession No. gi:18598041, NCBI Annotation Project, Feb. 7, 2002.
NCBI Accession No. gi:20553885, NCBI Annotation Project, May 13, 2002.

* cited by examiner

FIG. 1

CACGCGTCCGCCTGTCTCAAAAGAAAAAAAAAAAAAGGTGAAGCTGAACCCA
GATCTACACATACAGCTAATCTTACCAAAATGTGTGGAAGTAAAGCAATCTG
AAGGAAATTCAGTACCATACAATTTACTGACTGAAATACATCATATTGCTCA
TACTAAGAATAAGAGTGGAGAAGAATCATTTTTTTCCTGCTAAAATGATAGA
GGCAGAAGAGCAACAGCCTTGCAAGACAGACTTCTATTCTGAATTGCCAAAA
GTGGAACTTCATGCCCACTTGAATGGATCCATTAGTTCTCATACCATGAAGA
AATTAATAGCCCAGAAGCCAGATCTTAAAATCCACGATCAGATGACTGTGAT
TGACAAGGGAAAGAAAAGAACTTTGGAAGAATGTTTCCAGATGTTTCAAACT
ATTCATCAGCTTACTAGTAGCCCTGAAGATATTCTAATGGTCACAAAAGATG
TCATAAAAGAATTTGCAGATGACGGCGTCAAGTACCTGGAACTAAGGAGCAC
ACCCAGAAGAGAAATGCTACTGGAATGACTAAAAAGACTTATGTGGAATCT
ATACTTGAAGGTATAAAACAGTCCAAACAAGAAACTTGGACATTGATGTTA
GGTATTTGATAGCAGTTGACAGAAGAGGTGGCCCTTTAGTAGCCAAGGAGAC
TGTAAACTTGCCGAGGAGTTCTTCCTTTCTACTGAGGGTACAGTTCTTGGC
CTTGACCTCAGTGGAGACCCTACTGTAGGACAAGCAAAAGACTTCTTGGAAC
CTCTTTTAGAAGCTAAGAAAGCAGGTCTGAAGTTAGCATTGCATCTTTCAGA
GATTCCAAACCAAAAAAAAGAAACACAAATACTCCTGGATCTGCTTCCTGAC
AGAATCGGGCATGGAACATTTCTCAACTCCGGTGAGGGAGGATCCCTGGATC
TGGTGGACTTTGTGAGGCAACATCGGATACCACTGGGTAAGGCTTGGAGTTT
CAGGTCTTCCAGATGACTCTCTGTCTCTCCCCAATCCCCAGGTTGCCTGGG
GATTACAGAGAAGTACTGTTCTAAAAGTACGAATGTCATCTAGCTATTAAAA
GATGGAGTGTGTGCTTTCTGAGCCTTATTTAAAACAGAAAGCTTTAGCTTCC
ATTAGAATATAAGCTCTATGAGAGCAGGGCCCTGCTTGTCTTATTCGTTGT
TACATTCTCCAATGCTTGGAACTCAATAAGAATTTTTTAAAGGAATAAAGGG
TCATCTAGAATTTTAAAATGACTTTAACAAAATTGACATGTGTTATGAAAAT
ATGTAACATTATTTAAAAATTAAACATGGAAAATCCCAAGTAAAAAAAAAAA
AAAAA

FIG. 2

```
MIEAEEQQPCKTDFYSELPKVELHAHLNGSISSHTMKKLIAQKPDLKIHD
QMTVIDKGKKRTLEECFQMFQTIHQLTSSPEDILMVTKDVIKEFADDGVK
YLELRSTPRRENATGMTKKTYVESILEGIKQSKQENLDIDVRYLIAVDRR
GGPLVAKETVKLAEEFFLSTEGTVLGLDLSGDPTVGQAKDFLEPLLEAKK
AGLKLALHLSEIPNQKKETQILLDLLPDRIGHGTFLNSGEGGSLDLVDFV
RQHRIPLGKAWSFRSSR
```

FIG. 3

```
gi|4557249|ref|NP_000013.1||    MAQTPAFD---------KPKVELHVHLDGSIKPETILYYGRRRGIALPAN
gi|6680636|ref|NP_031424.1||    MAQTPAFN---------KPKVELHVHLDGAIKPETILYFGKKRGIALPAD
+3_ORF1                         MIEAEEQQPCKTDFYSELPKVELHAHLNGSISSHTMKKLIAQK----PDL
                                 *  ::      :        ****.:*:*...*:     ::      * gi|4557249|ref|NP_000013.1||    TAEGLLNVIGMDKPLTLPDFLAKFDYYMPAIAGCREAIKRIAYEFVEMKA
gi|6680636|ref|NP_031424.1||    TVEELRNIIGMDKPLSLPGFLAKFDYYMPVIAGCREAIKRIAYEFVEMKA
+3_ORF1                         KIHDQMTVIDKGKKRTLEECFQMFQTIHQLTS-SPEDILMVTKDVIKEFA
                                 . .    .:*. .*  :*    :  *:      :  . *    ::  :.::   * gi|4557249|ref|NP_000013.1||    KEGVVYVEVRYSPHLLANSKVEPIPWNQAEGDLTPDEVVALVGQGLQEGE
gi|6680636|ref|NP_031424.1||    KEGVVYVEVRYSPHLLANSKVDPMPWNQTEGDVTPDDVVDLVNQGLQEGE
+3_ORF1                         DDGVKYLELRSTP------------RRENATGMTKKTYVESILEGIKQSK
                                 . :**  *:*:*  :*.          .. :    .: .:*  .   *     : :*:::.:

gi|4557249|ref|NP_000013.1||    RD-FGVKARSILCCMRHQP----NWSPKVVELCKNYQQQTVVAIDLAGDE
gi|6680636|ref|NP_031424.1||    QA-FGIKVRSILCCMRHQP----SWSLEVLELCKKYNQKTVVAMDLAGDE
+3_ORF1                         QENLDIDVRYLIAVDRRGGPLVAKETVKLAEEFFLSTEGTVLGLDLSGDP
                                 :    :.:..*  ::. *:           . : ::  *        :  **:..**:**

gi|4557249|ref|NP_000013.1||    TIPGSSLLPGHVQAYQEAVKSGIHRTVHAGEVGSAEVVKEAVDILKTERL
gi|6680636|ref|NP_031424.1||    TIEGSSLFPGHVEAYEGAVKNGIHRTVHAGEVGSPEVVREAVDILKTERV
+3_ORF1                         TVGQAKDF---LEPLLEAKKAGLKLALHLSEIPNQKKETQILLDLLPDRI
                                 *:   :.. :   .::.    * *  *::  ::* .*:   . :      : :    *   .:*:

gi|4557249|ref|NP_000013.1||    GHGYHTLEDQALYNRLRQENMHFEICPWSSYLTGAWKPDTEHAVIRLKND
gi|6680636|ref|NP_031424.1||    GHGYHTIEDEALYNRLLKENMHFEVCPWSSYLTGAWDPKTTHAVVRFKND
+3_ORF1                         GHGTFLNSGEGGSLDLVDFVRQHRIP-----LGKAWSFRSSR--------
                                 ***    .   ..:.       *     .*    :.. ..   *   **.         . :::

gi|4557249|ref|NP_000013.1||    QANYSLNTDDPLIFKSTLDTDYQMTKRDMGFTEEEFKRLNINAAKSSFLP
gi|6680636|ref|NP_031424.1||    KANYSLNTDDPLIFKSTLDTDYQMTKKDMGFTEEEFKRLNINAAKSSFLP
+3_ORF1                         --------------------------------------------------
                                 :  :  . ::   :.    :   :  :.:         ::: :.  : :   :..

gi|4557249|ref|NP_000013.1||    EDEKRELLDLLYKAYGMPPSASAGQNL
gi|6680636|ref|NP_031424.1||    EEEKKELLERLYREYQ-----------
+3_ORF1                         ---------------------------
                                 :::::  :  .    .. ::
```

ADENOSINE DEAMINASE HOMOLOG

This application claims benefit to provisional application U.S. Ser. No. 60/226,786, filed Aug. 21, 2000; and to provisional U.S. Ser. No. 60/261,778, filed Jan. 16, 2001; under 35 U.S.C. 119(e).

FIELD OF THE INVENTION

The invention relates to nucleic acid and amino acid sequences of a novel adenosine deaminase (ADA) homolog and to the use of these sequences in treating adenosine deaminase deficiencies and in the development of agonists and antagonists of ADA function.

BACKGROUND OF THE INVENTION

Adenosine deaminase (ADA), an important enzyme of the purine salvage pathway, converts adenosine, deoxyadenosine and water into inosine and ammonia. Individuals who harbor deleterious mutations in the ADA gene can develop varying degrees of immunodeficiency disorder, from mild to severe Such immunodeficiency disorder is due to the toxic accumulation of the enzyme substrates, adenosine and deoxyadenosine, in the immature lymphoid cells. The onset of the disorder can also range from early childhood to adults, depending on the mutations inherited. Deficiencies of ADA are one of the leading causes of severe combined immunodeficiency disease (SCID) in children and is one of the leading targets for gene therapy approaches (R. Parkman et al., 2000, "Gene therapy for adenosine deaminase deficiency", *Ann. Rev. Med.*, 51:33–47).

The present invention relates to the isolation, characterization and use of a novel polynucleotide encoding a human adenosine deaminase homolog.

SUMMARY OF THE INVENTION

The present invention relates to a novel human adenosine deaminase homolog, hereinafter designated ADARP1 (adenosine deaminase related protein 1) and derivatives thereof.

The present invention also relates to a substantially purified ADARP1 protein or polypeptide having the amino acid sequence of SEQ ID NO: 2, or a functional portion thereof. In accordance with the present invention a substantially purified functional portion of ADARP1 is provided.

The present invention provides pharmaceutical compositions comprising at least one ADARP1 or functional portion thereof.

The present invention also provides methods for producing ADARP1 or a functional portion thereof.

One aspect of the present invention relates to isolated and substantially purified polynucleotides that encode ADARP1. In a particular aspect, the polynucleotide comprises the nucleotide sequence of SEQ ID NO: 1, and functional portion of ADARP1.

The invention also relates to a polynucleotide sequence comprising the complement of SEQ ID NO: 1 or variants thereof. In addition, the invention features polynucleotide sequences which hybridize under stringent or moderately stringent conditions to the polynucleotide sequence of SEQ ID NO: 1.

The invention further relates to nucleic acid sequences encoding polypeptides, oligonucleotides, fragments, portions or antisense molecules thereof, and expression vectors and host cells comprising polynucleotides that encode ADARP1.

It is another object of the present invention to provide methods for producing polynucleotide sequences encoding an ADARP1.

Another aspect of the invention are antibodies which bind specifically to an ADARP1 or epitope thereof, for use as therapeutics and diagnostic agents.

Another aspect of the invention is an agonist of an ADARP1. In addition, the present invention provides methods for screening for agonists of an ADARP1.

It is another object of the present invention to use the nucleic acid sequences, polypeptide, peptide and antibodies, including agonists, antagonists, and/or fragments thereof for diagnosis of disorders or diseases associated with ADA deficiencies, for gene therapy for correction of an ADA gene defect, for diagnosis and treatment of male reproductive disorders, testicular disorders, and musclo-skeletal disorders. The present invention also provides methods of preventing or treating disorders associated with ADA deficiencies and methods of regulating ADA expression in a mammal.

The present invention provides kits for detecting ADARP1 and for the screening and diagnosis of disorders associated with ADA deficiencies, male reproductive disorders, testicular disorders, and muscle-skeletal disorders.

BRIEF DESCRIPTION OF THE FIGURES

These and other objects, features and many of the attendant advantages of the invention will be better understood upon a reading of the detailed description of the invention when considered in connection with the accompanying drawings wherein:

FIG. 1 shows the ADARP1-encoding polynucleotide sequence (SEQ ID NO: 1) from the cDNA clone FL ⅔.

FIG. 2 shows the deduced amino acid sequence for ADARP1 (SEQ ID NO: 2).

FIG. 3 shows the alignment of the amino acid sequence of ADARP1 of clone FL ⅔ (+3. ORF1), (SEQ ID NO:2) to that of the protein sequence of human adenosine deaminase (gi 4557249), (SEQ ID NO:3) and to that of the mouse adenosine deaminase homolog (gi 6680636), (SEQ ID NO:4). In FIG. 3, the residues in bold letter type are those amino acid residues that are conserved among the human ADA gene, the mouse ADA gene and ADARP1, and that are known to be mutated in various forms of ADA-related immunodeficiencies (R. Parkman et al., 2000). Some of the residues in bold letter type are conserved amino acid residues that form the active site of the enzyme (Bhaumik et al., 1993 *J. Biol. Chem.*, 268:5464–5470). ADARP1 shows a truncation at the carboxy terminus of the protein.

DESCRIPTION OF THE INVENTION

Definitions

Figure 4:
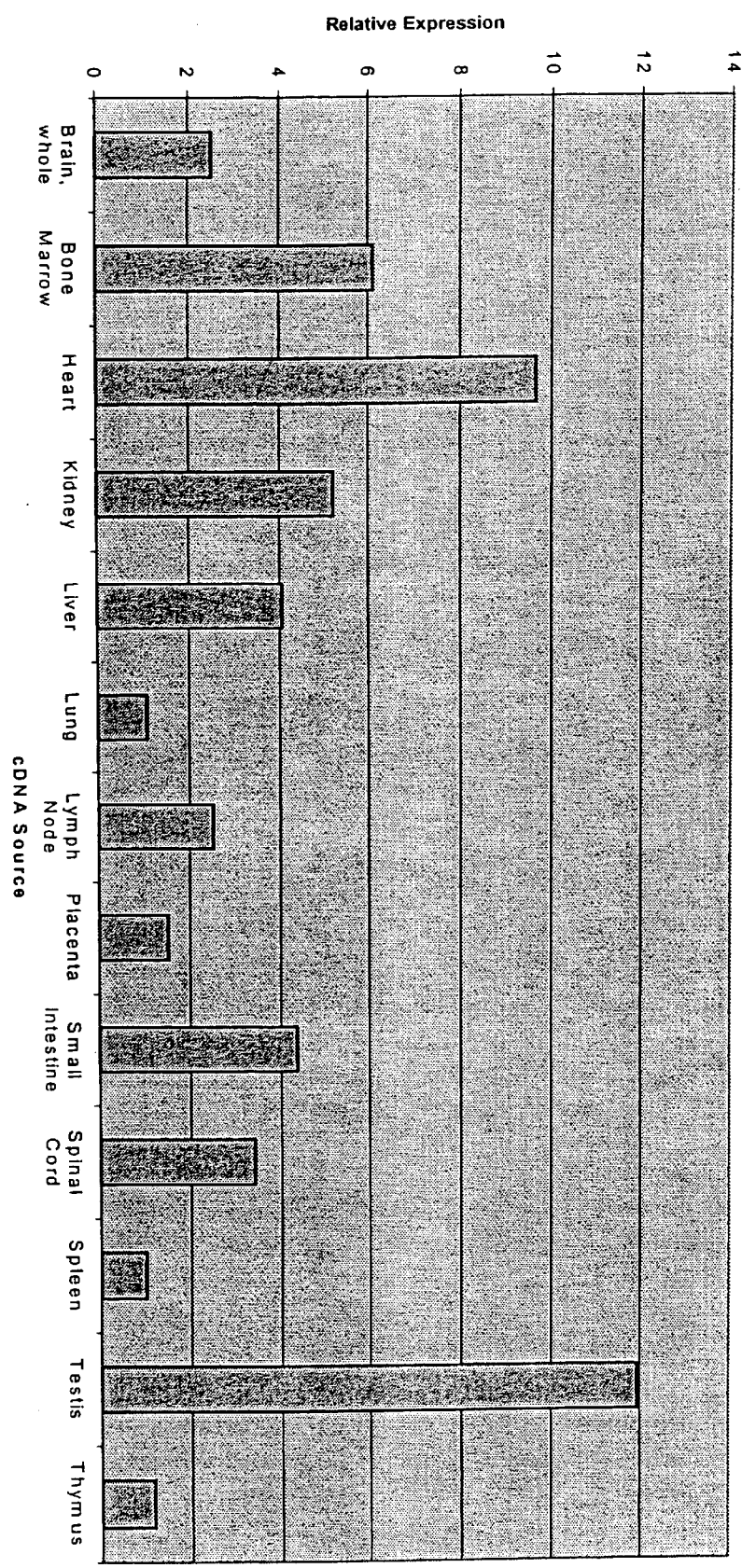
FIG. 4 shows the relative expression of transcripts corresponding to ADARP1 is various tissues.
Figure 5:
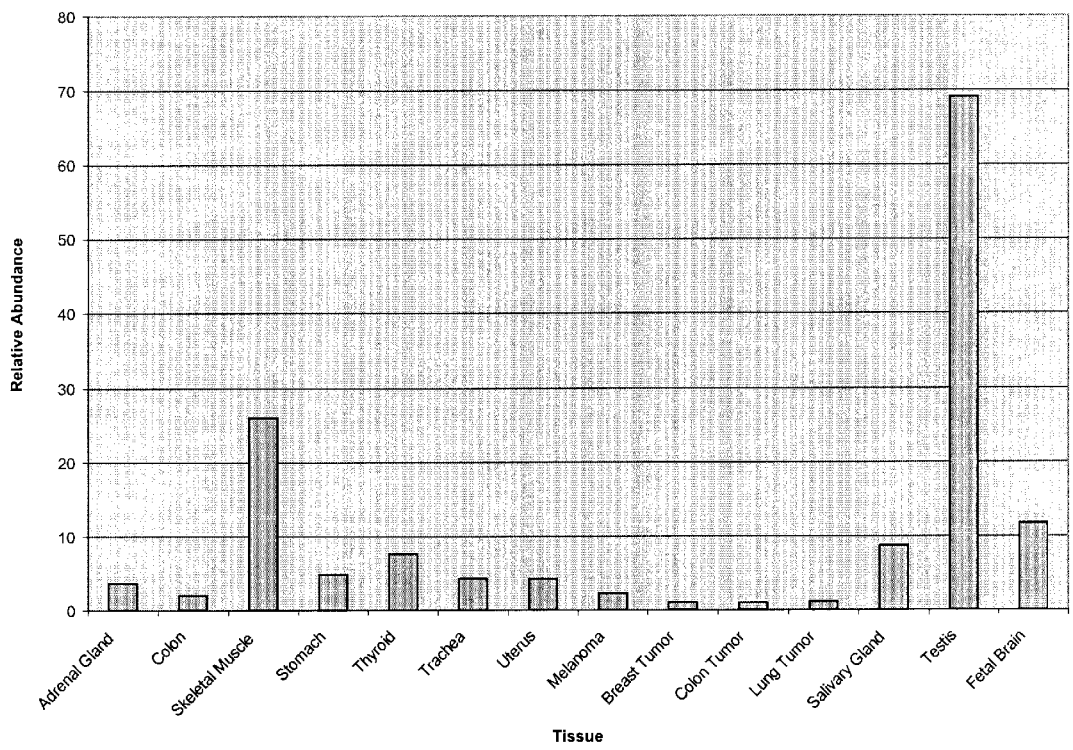
FIG. 5 shows the relative expression profiling of ADARP1 in additional tissues.

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al (1993) *Anticancer Drug Des.,* 8:53–63).

ADARP1, as used herein, refers to the amino acid sequence of the substantially purified adenosine deaminase protein homolog obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR (PE Biosystems, Norwalk, Conn.) in the 5' and/or the 3' direction and resequenced, or which as been assembled from the overlapping sequences of more than one Incyte clone or publicly available clone using the GELVIEW Fragment Assembly system (GCG, Madison, Wis.), or which has been both extended and assembled.

A "variant" of ADARP1, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic ADARP1, or any oligopeptide thereof, to induce a specific immune response in appropriate animals or cells and to bind with specific antibodies.

The term "agonist", as used herein, refers to a molecule which increases the amount of, or prolongs the duration of, the activity of ADARP1 or ADA. Agonists may include proteins, nucleic acids, carbohydrates, organic molecules or any other molecules.

The term "mimetic", as used herein, refers to a molecule, the structure of which is developed from knowledge of the structure of ADARP1 or portions thereof and, as such, is able to effect some or all of the actions of ADARP1.

The term "derivative", as used herein, refers to the chemical modification of a nucleic acid encoding ADARP1 or the encoded ADARP1. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% or greater free from other components with which they are naturally associated.

"Amplification", as used herein, refers to the production of additional copies of a nucleic acid sequence and is generally carried out using polymerase chain reaction (PCR) technologies well known in the art (Dieffenbach, D. W. and G. S. Dveksler (1995), *PCR Primer, a Laboratory Manual,* Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., $C_o t$ or $R_o t$ analysis) or between one nucleic acid sequence present in solution and another nucleic acid sequence immobilized on a solid support (e.g., membranes, filters, chips, pins or glass slides to which cells have been fixed in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective)

interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low, moderate, or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low, moderate, or high stringency different from, but equivalent to, the above listed conditions.

The phrase stringency of hybridization refers to conditions under which polynucleic acid hybrid molecules are stable. As known to those skilled in the art, the stability of a hybrid is reflected in the melting temperature ($T_m$) of the hybrids. The term "stringent conditions", as used herein, is the "stringency" which occurs within a range from about Tm-5° C. (5° C. below the melting temperature $T_m$ of the probe) to about 20° C. to 25° C. below Tm. As will be understood by those of skill in the art, the stringency of hybridization may be altered in order to identify or detect identical or related polynucleotide sequences. As will be further appreciated by the skilled practitioner, Tm can be approximated by the formulas as known in the art, depending on a number of parameters, such as the length of the hybrid or probe in number of nucleotides, or hybridization buffer ingredients and conditions (See, for example, T. Maniatis et al., *Molecular Cloning: A Laboratory Manual*, Cold Spring Harbor Laboratory, Cold Spring Harbor, N.Y., 1982 and J. Sambrook et al., *Molecular Cloning: A Laboratory Manual*, Cold Spring Harbor Laboratory, Cold Spring Harbor, N.Y., 1989; *Current Protocols in Molecular Biology*, Eds. F. M. Ausubel et al., Vol. 1, "Preparation and Analysis of DNA", John Wiley and Sons, Inc., 1994–1995, Suppls. 26, 29, 35 and 42; pp. 2.10.7–2.10.16; G. M. Wahl and S. L. Berger (1987; *Methods Enzymol.* 152:399–407); and A. R. Kimmel, 1987; *Methods of Enzymol.* 152:507–511). As a general guide, $T_m$ decreases approximately 1° C.–1.5° C. with every 1% decrease in sequence homology. Also, in general, the stability of a hybrid is a function of sodium ion concentration and temperature. Typically, the hybridization reaction is initially performed under conditions of low stringency, followed by washes of varying, but higher stringency. Reference to hybridization stringency, e.g., high, moderate, or low stringency, typically relates to such washing conditions.

Thus, by way of nonlimiting example, high stringency refers to conditions that permit hybridization of those nucleic acid sequences that form stable hybrids in 0.018M NaCl at about 65° C. (i.e., if a hybrid is not stable in 0.018M NaCl at about 65° C., it will not be stable under high stringency conditions). High stringency conditions can be provided, for instance, by hybridization in 50% formamide, 5× Denhart's solution, 5× SSPE (1× SSPE buffer comprises 0.15 M NaCl, 10 mM $Na_2HPO_4$, 1 mM EDTA), (or 1× SSC buffer containing 150 mM NaCl, 15 mM $Na_3$ citrate.2 $H_2O$, pH 7.0), 0.2% SDS at about 42° C., followed by washing in 133 SSPE (or SSC) and 0.1% SDS at a temperature of at least about 42° C., preferably about 55° C., more preferably about 65° C.

Moderate stringency refers, by nonlimiting example, to conditions that permit hybridization in 50% formamide, 5× Denhart's solution, 5× SSPE (or SSC), 0.2% SDS at 42° C. (to about 50° C.), followed by washing in 0.2× SSPE (or SSC) and 0.2% SDS at a temperature of at least about 42° C., preferably about 55° C., more preferably about 65° C.

Low stringency refers, by nonlimiting example, to conditions that permit hybridization in 10% formamide, 5× Denhart's solution, 6× SSPE (or SSC), 0.2% SDS at 42° C., followed by washing in 1× SSPE (or SSC) and 0.2% SDS at a temperature of about 45° C., preferably about 50° C.

For additional stringency conditions, see T. Maniatis et al., *Molecular Cloning: A Laboratory Manual*, Cold Spring Harbor Laboratory, Cold Spring Harbor, N.Y. (1982). It is to be understood that the low, moderate and high stringency hybridization/washing conditions may be varied using a variety of ingredients, buffers and temperatures well known to and practiced by the skilled practitioner.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO: 2" encompasses the full-length human ADARP1 and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and partial bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to an antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding ADARP1 or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO: 1 by northern analysis is indicative of the presence of mRNA encoding ADARP1 in a sample and thereby correlates with expression of the transcript from the polynucleotide encoding the protein.

"Alterations" in the polynucleotide of SEQ ID NO: 1, as used herein, comprise any alteration in the sequence of polynucleotides encoding ADARP1 including deletions, insertions, and point mutations that may be detected using hybridization assays. Included within this definition is the detection of alterations to the genomic DNA sequence which encodes ADARP1 (e.g., by alterations in the pattern of restriction fragment length polymorphisms capable of hybridizing to SEQ ID NO: 1), the inability of a selected fragment of SEQ ID NO: 1 to hybridize to a sample of genomic DNA (e.g., using allele-specific oligonucleotide probes), and improper or unexpected hybridization, such as hybridization to a locus other than the normal chromosomal locus for the polynucleotide sequence encoding ADARP1 (e.g., using fluorescent in situ hybridization (FISH) to metaphase chromosome spreads).

As used herein, the term "antibody" refers to intact molecules as well as fragments thereof, such as Fab, F(ab')$_2$, Fv, chiimeric antibody, single chain antibody which are capable of binding the epitopic determinant. Antibodies that bind ADARP1 polypeptides can be prepared using intact polypeptides or fragments containing small peptides of interest or prepared recombinantly for use as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g, a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The present invention provides a novel human adenosine deaminase homolog designated herein as adenosine deaminase related protein (ADARP1), the polynucleotides encoding ADARP1, and the use of these compositions for the diagnosis, prevention, or treatment of disorders associated with adenosine deaminase deficiencies such as immunodeficiencies including severe combined immunodeficiency disease (SCID).

Nucleic acids encoding human ADARP1 of the present invention were first identified in an Incyte EST Clone ID:877185 and public domain EST Clone ATCC 3246386 using Basic Local Alignment Search Tool (BLAST) analysis for similarity with a published human adenosine deaminase sequence (Example 1).

In one embodiment, the invention encompasses a polypeptide comprising the amino acid sequence of SEQ ID NO: 2 as shown in FIG. 2 and functional portions thereof. ADARP1 shares chemical and structural homology with the human ADA and a murine homolog as illustrated in FIG. 3.

The invention also encompasses ADARP1 variants. A preferred ADARP1 variant is one having at least 80%, and more preferably 90% or greater, amino acid identity to the ADARP1 amino acid sequence of SEQ ID NO: 2. A most preferred ADARP1 variant is one having at least 95% amino acid sequence identity to SEQ ID NO: 2.

The present invention provides isolated ADARP1 and homologs thereof having ADA activity. Such proteins are substantially free of contaminating endogenous materials. Derivatives of the ADARP1 within the scope of the invention also include various structural forms of the primary protein which retain biological activity. Due to the presence of ionizable amino and carboxyl groups, for example, an ADARP1 protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini.

The present invention further encompassed fusion proteins comprising the amino acid sequence of an ADARP1 or portion thereof linked to an immunoglobulin Fc region. An exemplary Fc region is a human IgGl comprising the hinge region, $CH_2$ and $CH_3$ domains of an Fc region of human IgGI. Depending on the portion of the Fc region used, a fusion protein may be expressed as a dimer, through formation of interchain disulfide bonds. If the fusion proteins are made with both heavy and light chains of an antibody, it is possible to form a protein oligomer with as many as four ADARP1 regions.

The invention also encompasses polynucleotides which encode ADARP1. Accordingly, any nucleic acid sequence which encodes the amino acid sequence of ADARP1 can be used to generate recombinant molecules which express ADARP1. In particular embodiment, the invention encompasses the polynucleotide comprising the nucleic acid sequence of SEQ ID NO. 1 as shown in FIG. 1.

It will be appreciated by those skilled in the art that as a result of the degeneracy of the genetic code, a multitude of nucleotide sequences encoding ADARP1, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring ADARP1, and all such variations are to be considered as being specifically disclosed.

Although nucleotide sequences which encode ADARP1 and its variants are preferably capable of hybridizing to the nucleotide sequence of the naturally occurring ADARP1 under appropriately selected conditions of stringency, it may be advantageous to produce nucleotide sequences encoding ADARP1 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding ADARP1 and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode ADARP1 and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding ADARP1 or any portion thereof.

Also encompassed by the invention are polynucleotide sequences that are capable of hybridizing to the claimed nucleotide sequences, and in particular, those shown in SEQ ID NO: 1, under various conditions of stringency. Hybridization conditions are based on the melting temperature (Tm) of the nucleic acid binding complex or probe, as taught in Wahl, G. M. and S. L. Berger (1987; *Methods Enzvmol.* 152:399–407) and Kimmel, A. R. (1987; *Methods of Enzymol.* 152:507–511), and may be used at a defined stringency. In one embodiment, sequences include those capable of hybridizing under moderately stringent conditions (prewashing solution of 2× SSC, 0.5% SOS, 1.0 mM MEDTA, pH 8.0) and hybridization conditions of 50° C., 5× SSC, overnight, to the sequences encoding ADARP1 and other sequences which are degenerate to those which encode the ADARP1.

Altered nucleic acid sequences encoding ADARP1 which are encompassed by the invention include deletions, insertions, or substitutions of different nucleotides resulting in a polynucleotide that encodes the same or a functionally equivalent ADARP1. The encoded protein may also contain deletions, insertions, or substitutions of amino acid residues which produce a silent change and result in a functionally equivalent ADARP1. Deliberate amino acid substitutions may be made on the basis of similarity in polarity, charge, solubility, hydrophobicity, hydrophilicity, and/or the amphipathic nature of the residues as long as the biological activity of ADARP1 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding ADARP1. As used herein, an "allele" or "allelic sequence" is an alternative form of the gene which may result from at least one mutation in the nucleic acid sequence. Alleles may result in altered mRNAs or poypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENCE (US Biochemical Corp. Cleveland, Ohio), Taq polymerase (PE Biosystems), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (PE Biosystems).

The nucleic acid sequences encoding ADARP1 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) *PCR Methods Applic.* 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) *Nucleic Acids Res.* 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) *PCR Methods Applic.* 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; *Nucleic Acids Res.* 19:3055–3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g., GENOTYPER and SEQUENCE NAVIGATOR, PE Biosystems) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode or fusion proteins or functional equivalents thereof, may be used in recombinant DNA molecules to direct expression of ADARP1 in appropriate host cells. Due to the inherent degeneracy of the genetic code, other DNA sequences which encode substantially the same or a functionally equivalent amino acid sequence may be produced and these sequences may be used to clone and express ADARP1.

As will be understood by those of skill in the art, it may be advantageous to produce ADARP1-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter ADARP1 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding ADARP1 may be ligated to a heterologous sequence to encode a fusion protein. A fusion protein may also be engineered to contain a cleavage site located between the ADARP1 encoding sequence and the heterologous protein sequence, so that ADARP1 may be cleaved and purified away from the heterologous moiety.

In another embodiment, sequences encoding ADARP1 may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of ADARP1, or a portion thereof. For example, peptide synthesis can be performed using various solid-phase techniques (Roberge, J. Y. et al. (1995) Science 269:202–204) and automated synthesis may be achieved, for example, using the ABI 43 1A Peptide Synthesizer (PE Biosystems).

The newly synthesized peptide may be substantially purified by preparative high performance liquid chromatography (e.g., Creighton, T. (1983) Proteins, Structures and Molecular Principles, WH Freeman and Co., New York, N.Y), by reversed-phase high performance liquid chromatography, or other purification methods as are known in the art. The composition of the synthetic peptides may be confirmed by amino acid analysis or sequencing (e.g., the Edman degradation procedure; Creighton, supra). Additionally, the amino acid sequence of ADARP1, or any part thereof, may be altered during direct synthesis and/or combined using chemical methods with sequences from other proteins, or any part thereof, to produce a variant polypeptide.

In order to express a biologically active ADARP1 the nucleotide sequences encoding ADARP1 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding ADARP1. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus. TMV) or with bacterial expression vectors (e.g., Ti or pBR322 plasmids); or animal cell systems.

The "control elements" or "regulatory sequences" are those non-translated regions of the vector-enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (Gibco BILL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding ADARP1, vectors based on SV40 or EBV may be used with an appropriate selectable marker.

In bacterial systems, a number of expression vectors may be selected depending upon the use intended for ADARP1. For example, when large quantities of are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding ADARP1 may be ligated into the vector in frame with sequences for the amino-terminal Met and the subsequent 7 residues of β-galactosidase so that a hybrid protein is produced, pIN vectors (Van Heeke, G. and S. M. Schuster (1989) *J. Biol. Chem.* 264:5503–5509); and the like. pGEX vectors (Promega, Madison, Wis.) may also be used to express foreign polypeptides, as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544.

In cases where plant expression vectors are used, the expression of sequences encoding ADARP1 may be driven by any of a number of promoters. For example, viral promoters such as the 35S and 19S promoters of CaMV may be used alone or in combination with the omega leader sequence from TMV (Takamatsu, N. (1987) *EMBO J.* 6:307–311). Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probl. Cell Differ.* 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express ADARP1 as reported by Bhaumik et al. (1993, *J. Biol. Chem.*, 268:5464–5470) for human ADA. For example, in one such system, *Autographa californica* nuclear polyhedrosis virus (AcNPV) is used as a vector to express foreign genes in *Spodoptera frugiperda* cells or in Trichoplusia larvae. The sequences encoding ADARP1 may be cloned into a non-essential region of the virus such as the polyhedrin gene, and placed under control of the polyhedrin promoter. Successful insertion of ADARP1 will render the polyhedrin gene inactive and produce recombinant virus lacking coat protein. The recombinant viruses may then be used to infect, for example, *S. frugiperda* cells or Trichoplusia larvae in which ADARP1 may be expressed (Engelhard, E. K. et al. (1994) *Proc. Nat. Acad. Sci.* 91:3224–3227).

In mammalian host cells, a number of viral-based expression systems may be utilized. In cases where an adenovirus is used as an expression vector, sequences encoding ADARP1 may be ligated into an adenovirus transcription/translation complex consisting of the late promoter and tripartite leader sequence. Insertion in a non-essential E1 or E3 region of the viral genome may be used to obtain a viable virus which is capable of expressing ADARP1 in infected host cells (Logan, J. and Shenk, T. (1984) *Proc. Natl. Acad. Sci.* 81:3655–3659). In addition, transcription enhancers, such as the Rous, sarcoma virus (RSV) enhancer, may be used to increase expression in mammalian host cells.

Specific initiation signals may also be used to achieve more efficient translation of sequences encoding ADARP1. Such signals include the ATG initiation codon and adjacent sequences. In cases where sequences encoding ADARP1, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express ADARP1 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1980) *Cell* 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides, neomycin and G-418 (Colbere-Garapin, F. et al (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisd), which allows cells to utilize histinol in place of histidine (Hartman, S. C. and R. C. Mulligan (1988) *Proc. Natl. Acad. Sci.* 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding ADARP1 is inserted within a marker gene sequence, recombinant cells containing sequences encoding can be identified by the absence of marker gene function. Alternatively, a marker gene can be placed in tandem with a sequence encoding ADARP1 under the control of a single promoter. Expression of the marker gene in response to induction or selection usually indicates expression of the tandem gene as well.

Alternatively, host cells which contain the nucleic acid sequence encoding ADARP1 and express ADARP1 may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding ADARP1 can be detected by DNA-DNA or DNA-RNA hybridization or amplification using probes or portions or fragments of polynucleotides encoding ADARP1. Nucleic acid amplification based assays involve the use of oligonucleotides or oligomers based on the sequences encoding ADARP1 to detect transformants containing DNA or RNA encoding ADARP1. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of ADARP1, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on ADARP1 is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding ADARP1 include oligolabeling, nick translation, end-labeling or PCR amplification using a labeled nucleotide. Alternatively, the sequences encoding ADARP1, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kit (Amersham Pharmacia Biotech, Piscataway, N.J.); Promega (Madison Wis.); and U.S. Biochemical Corp., (Cleveland, Ohio)). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding ADARP1 may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode ADARP1 may be designed to contain signal sequences which direct secretion of ADARP1 through a prokaryotic or eukaryotic cell membrane.

In addition to recombinant production, fragments of ADARP1 may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using Applied Biosystems 431A Peptide Synthesizer (PE Biosystems). Various fragments of ADARP1 be chemically synthesized separately and combined using chemical methods to produce the full length molecule.

Therapeutics

Chemical and structural homology exists among ADARP1, human ADA, and murine ADA. Furthermore, ADARP1 is expressed in human tissues, many of which are associated with lymphoid development and differentiation ADARP1, therefore appears to be a homolog of human ADA and plays a role in lymphoid cell development and function. Expression of ADARP1 in testes and skeletal muscle indicates a role for ADARP1 in testes and musclo-skeletal development and function.

ADARP1 can be administered for the purpose of preventing or treating ADA deficiency and the diseases associated with ADA deficiency. ADARP1 can also be administered for the purpose of enhancing or ameliorating immune responses, in particular, T lymphocyte and B lymphocyte development, differentiation and function in mammals, preferably humans. ADARP1 may be modified using polyethylene glycol (PEG) as known in the art (Hershfield et al 1987, *New Engl. J. Med.* 316:589–596) to enhance the half-life of ADARP1 upon administration.

In another embodiment a vector capable of expressing ADARP1, or a fragment or derivative thereof, may also be administered to a subject to treat or prevent a ADA deficiency and associated immunodeficiency diseases.

Gene therapy for ADA deficiencies have been reported in the art using human ADA or human ADA minigenes. The techniques reported therein may be employed for the gene therapy using the ADARP1 gene. (Blaese et al., 1995, *Science* 270:475–480; U.S. Pat. No. 5,399,346; Bordignon et al., 1995, *Science* 270:470–475; and Onodera et al., 1998, *Blood* 91:30–36.)

Polynucleotides and polypeptides, including agonists, antagonists, and/or fragments thereof may be administered for the prevention or treatment of male reproductive disorders, testicular disorders, and musclo-skeletal disorders.

In other embodiments, any of the therapeutic proteins, agonists, mimetics, nucleic acid sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

In another embodiment of the invention, the polynucleotides encoding ADARP1, or any fragment thereof may be used for therapeutic purposes.

Expression vectors derived from retroviruses, adenovirus, herpes virus, non-replicating or genetically engineered human immunodeficiency virus (HIV) vectors, or vaccinia virus, or from various bacterial plasmids may be used for delivery of nucleotide sequences to the targeted organ, tissue or cell population. Methods which are well known to those skilled in the art can be used to construct recombinant vectors which will express the ADARP1 polynucleotide and its encoded ADARP1 product. These techniques are described both in J. Sambrook et al. (supra) and in F. M. Ausubel et al. (supra).

Many methods for introducing vectors into cells or tissues are available for use in vivo, in vitro, and ex vivo. For ex vivo therapy, vectors may be introduced into stem cells taken from the patient and clonally propagated for autologous transplant back into that same patient as disclosed in U.S. Pat. Nos. 5,399,493 and 5,437,994. Delivery by transfection and by liposome injections may be achieved using methods which are well known in the art. Also microparticle bombardment using naked DNA or gene delivery vectors as immunogen is suitable for introducing ADARP1-encoding DNA into cells. Techniques for gene delivery employing vectors or naked DNA are known to the skilled practitioner in the art.

REFERENCE

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of ADARP1, PEG-modified ADA, mimetics, agonists of ADARP1 and/or combinations thereof. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs, hormones, or biological response modifiers.

The pharmaceutical compositions utilized in this invention may be administered by any number of routes including, but not limited to, oral, intravenous, intramuscular, intraarterial, intramedullary, intrathecal, intraventricular, transdermal, subcutaneous. intraperitoneal, intranasal, enteral, topical, sublingual, or rectal means.

In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth, and proteins such as gelatin and collagen. If desired, disintegrating or solubilizing agents may be added, such as the cross-linked polyvinyl pyrrolydone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of ADARP1, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

A therapeutically effective dose refers to that amount of active ingredient, for example ADARP1 or fragments thereof, or agonists of ADARP1 which ameliorates the symptoms or condition of ADA deficiency.

A therapeutically effective dose may also refer to that amount of polynucleotide or polypeptide, including agonists, antagonists, and/or fragments thereof useful in the prevention or treatment of male reproductive disorders, testicular disorders or musclo-skeletal disorders.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 microgram, up to a total dose of about 1 g, depending upon the route of administration. Guidance as to particular dosages and methods of delivery is provided in the literature and generally available to practitioners in the art. In the case of gene therapy, in addition to administration of a vector expressing ADARP1, the individual may additionally be administered ADARP1 or functional fragments thereof, PEG modified-ADARP1, agonist, mimetic or combinations thereof.

Antibodies specific for ADARP1 may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with or any fragment or oligopeptide thereof which has immunogenic properties. Depending on the host species, various adjuvants may be used to increase immunological response. Such adjuvants include, but are not limited to, Ribi adjuvant R700 (Ribi, Hamilton, Montana), incomplete Freund's adjuvant, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacillus Calmette Guerin) and *Corynebacterium parvumn* are especially preferable.

It is preferred that the peptides, fragments, or oligopeptides used to induce antibodies to ADARP1 have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. The peptides, fragments or oligopeptides may comprise a single epitope or antigenic determinant or multiple epitopes. Short stretches of ADARP1 amino acids may be fused with those of another protein such as keyhole limpet hemocyanin and antibody produced against the chimeric molecule.

Monoclonal antibodies to ADARP1 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) *Nature* 256:495–497; Kozbor, D. et al. (1985) *J. Immunol. Methods* 81:31–42, Cote, R. J. et al. (1983) *Proc. Natl. Acad. Sci.* 80:2026–2030; Cole, S. P. et al. (1984) *Mol. Cell Biol.* 62:109–120).

In addition, techniques developed for the production of "chimeric antibodies," the splicing of mouse antibody genes to human antibody genes to obtain a molecule with appropriate antigen specificity and biological activity can be used (Morrison, S. L. et al. (1984) *Proc. Natl. Acad. Sci.* 81:6851–6855; Neuberger, M. S. et al. (1984) *Nature* 312:604–608; Takeda, S. et al. (1985) *Nature* 314:452–454). Alternatively, techniques described for the production of single chain antibodies may be adapted, using methods known in the art, to produce ADARP1-specific single chain antibodies. Antibodies with related specificity, but of distinct idiotypic composition, may be generated by chain shuffling from random combinatorial immunoglobulin libraries (Burton D. R. (1991) *Proc. Natl. Acad. Sci.* 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) *Proc. Natl. Acad. Sci.* 86:3833–3837; Winter, G. et al. (1991) *Nature* 349:293–299).

Antibody fragments which contain specific binding sites for ADARP1 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) *Science* 254.1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between ADARP1 and its specific antibody. A two-site, monoclonal-based immunoassay utilizing monoclonal antibodies reactive to two non-interfering ADARP1 epitopes is preferred, but a competitive binding assay may also be employed (Maddox, supra).

Diagnostics

In another embodiment of the present invention, antibodies which specifically bind ADARP1 may be used for the diagnosis of ADA deficiencies, diagnosis of disorders of the male reproductive tract, diagnoses of musclo-skeletal disorders, or used in assays to monitor patients being treated with ADARP1, agonists or antagonists thereof. Diagnostic assays for ADA deficiencies include methods which utilize the antibody and a label to detect it in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

In another embodiment of the invention, the polynucleotides encoding ADARP1 may be used for diagnostic purposes. The polynucleotides which may be used include oligonucleotide sequences, antisense RNA and DNA molecules, and PNAs. The polynucleotides may be used to detect and quantify gene expression in biopsied tissues. The diagnostic assay may be used to distinguish between absence, presence, and excess expression of ADARP1, and to monitor regulation of ADARP1 levels during therapeutic intervention.

In one aspect, hybridization with PCR probes which are capable of detecting polynucleotide sequences, including genomic sequences, encoding ADARP1 or closely related molecules, may be used to identify nucleic acid sequences which encode ADARP1. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding ADARP1, alleles, or related sequences.

Probes may also be used for the detection of related sequences, and should preferably contain at least 50% of the nucleotides from any of the ADARP1 encoding sequences. The hybridization probes of the subject invention may be DNA or RNA and derived from the nucleotide sequence of SEQ ID NO: 1 or from genomic sequence including promoter, enhancer elements, and introns of the naturally occurring ADARP1.

EXAMPLES

The Examples below are provided to illustrate the subject invention and are not intended to limit the invention.

Example I

Bioinformatics Analysis

Human adenosine receptor protein sequences were used as probes to search the Incyte and public domain EST databases. The search program used was gapped BLAST (S. F. Altschul et al., 1997, "Gapped BLAST and PSI-BLAST: a new generation of protein database search programs", *Nucleic Acid Res.*, 25, 3389–3402. The top EST hits from the BLAST results (i.e., those having the highest homology) were searched back against the non-redundant protein and patent sequence databases. From this analysis, ESTs encoding a potential novel adenosine deaminase were identified based on sequence homology with human adenosine deaminase. An Incyte EST (CloneID: 877185) and a public domain EST (ATCC-3246386) were selected as a potential novel adenosine deaminase candidate nucleic acid for subsequent analysis.

Extension of the EST Sequence

A PCR primer pair, designed from the DNA sequence from ATCC clone 3246386 was used to amplify a piece of DNA from the clone in which the antisense strand of the amplified fragment was biotinylated on the 3' end. The sequences of the two primers used to generate the probe utilized to clone the full length sequence of the ADA homolog ADARP1 are as follows:

sense PCR primer: 5'-ACGAGGAGCAATCTGAAGGAAA-3' (SEQ ID NO:5) and biotinylated antisense PCR primer:

5'-bTCATGGTATGAGAACTAATGGATCCA-3', (b=biotin), (SEQ ID NO:6)

designed from the DNA sequence of ATCC clone 3246386.

The biotinylated piece of double-stranded DNA was denatured and hybridized at 42° C. to a mixture of single-stranded covalently closed circular cDNA libraries in 50% formamide, 1.5 M NaCl, 40 mM $NaPO_4$, pH 7.2, 5 mM EDTA and 0.2% SDS which contained DNA corresponding to the sense strand. The cDNA library was converted to single stranded molecules by infecting a rapidly growing bacterial culture with fl helper phage, followed by purification of the DNA by standard methods. Hybrids between the biotinylated DNA and the circular cDNA were captured on streptavidin magnetic beads. (D. A. Tagle et al., 1993, *Nature*, 361:751–753).

Upon thermal release of the cDNA from the biotinylated DNA, the single stranded cDNA was converted into double strands using a primer homologous to a T7 sequence on the cDNA cloning vector. The double stranded cDNA was introduced into *E. coli* by electroporation and the resulting colonies were screened by PCR using the original primer pair to identify the proper cDNA sequence. Individual cDNAs were obtained for both the above-described Incyte and ATCC probes. Sequence analysis determined that both the Incyte and ATCC clones were from one and the same cDNA sequence. One clone named FL2/3 was sequenced on both strands (FIG. 1), (SEQ ID NO: 1). The isolated FL2/3 clone containing the full-length DNA sequence of ADARP1 according to the present invention was deposited at the American Type Culture Collection (ATCC), 10801 University Boulevard, Manassas, Va. 20110–2209 on Nov. 15, 2000 under ATCC Accession No. PTA-2678 according to the terms of the Budapest Treaty.

The deduced amino acid sequence of the fall length clone FL⅔ DNA sequence is shown in FIG. 2, (SEQ ID NO:2).

An alignment of the amino acid sequence of partial clone FL⅔ (+3_ORF1) to that of the protein sequence of human adenosine deaminase (gi 4557249), (SEQ ID NO:3), and the mouse adenosine deaminase homolog (gi 6680636), (SEQ ID NO:4), is shown in FIG. 3.

Example II

Expression Profiling of ADA homolog ADARP1

The same PCR primer used in the cloning of ADARP1 was used to measure the steady state levels of mRNA by quantitative PCR. Briefly, first strand cDNA was made from commercially available tissue-derived mRNA. The relative amount of cDNA used in each assay was determined by performing a parallel experiment using a primer pair for the cyclophilin gene which is expressed in equal amounts in all tissues. The cyclophilin primer pair detected small variations in the amount of cDNA in each sample and these data were used for normalization of the data obtained with the primer pair for ADARP1. The PCR data were converted into a relative assessment of the difference in transcript abundance among the tissues tested. The data from this analysis are presented in FIG. 4. As demonstrated in FIG. 4, transcripts corresponding to ADARP1 were found in all tissues, with the highest amount detected in the heart and the lowest amount detected in the lung and spleen.

Example III

Expression Profiling of ADARP1 in Additional Tissues

Specific method for ADARP1

Quantitative PCR

I. Determine Number of rxns and Amount of Mix Needed
  A. all samples run in triplicate, so sample tubes need 3.5 rxns worth of mix
  B. =(2× # tissue samples+1 no template control+1 for pipetting error)(3.5)
II. Rxn Mix

| Components | vol/rxn |
| --- | --- |
| 2X SybrGreen Master Mix | 25 microliters |
| water | 23.5 microliters |
| primer mix (10 uM ea.) | 0.5 microliters |
| cDNA (2.5 ng/uL) | 1 microliter |

A. Make mix minus cDNA for enough reactions as determined above
  B. Aliquot 171.5 uL of mix to sample tubes
  C. Add 1 uL of cDNA to each sample tube
  D. Mix gently and spin down to collect
  E. Aliquot 3×50 uL to optical plate
III. Set Up 5700
  A. Enter primer and sample set-up
  B. Save (plate) As . . .
  C. Run default program including dissociation protocol (check box)
  D. Save again immediately after run (before trying to analyze data)
IV. Analyze Data
  A. Set threshold in Log view to intersect linear region of amplification
  B. Set background in Linear view to 2–3 cycles before amplification curve appears
  C. Click Analyze
  D. Export Report to disk in floppy A: drive
  E. Calculate mean values for RT+
  F. Normalize to Cyclophilin: dCt=sample mean−cyclophilin mean
  G. Determine ddCt by subtracting individual dCts from the highest value of dCt in the list H. Determine Relative Abundance by formula $2^{\wedge}ddCt$.

Expression profiling in 12 additional tissue RNA was carried out to further refine the overall pattern of gene expression in the body. The same PCR primer pair that was used to identify ADARP1 (also referred to Incyte-877185 or FL2) cDNA clones was used to measure the steady state levels of mRNA by quantitative PCR.

```
Incyte-877185-s
CGGCGTCAAGTACCTGGAA (SEQ ID NO: 7)

Incyte-877185-ab
bTCGGCAAGTTTTACAGTCTCCTT (SEQ ID NO: 8)
```

Briefly, first strand cDNA was made from commercially available mRNA (Clontech, Stratagene, and LifeTechnologies) and subjected to real time quantitative PCR using a PE 5700 instrument (Applied Biosystems, Foster City, Calif.) which detects the amount of DNA amplified during each cycle by the fluorescent output of SYBR green, a DNA binding dye specific for double strands. The specificity of the primer pair for its target is verified by performing a thermal denaturation profile at the end of the run which gives an indication of the number of different DNA sequences present by determining melting Tm. In the case of the ADARP1 primer pair, only one DNA fragment was detected having a homogeneous melting point. Contributions of contaminating genomic DNA to the assessment of tissue abundance is controlled for by performing the PCR with first strand made with and without reverse transcriptase. In all cases, the contribution of material amplified in the no reverse transcriptase controls was negligible.

Small variations in the amount of cDNA used in each tube was determined by performing a parallel experiment using a primer pair for a gene expressed in equal amounts in all tissues, cyclophilin. These data were used to normalize the data obtained with the ADARP1 primer pair. The PCR data was converted into a relative assessment of the difference in transcript abundance amongst the tissues tested and the data are presented in bar graph form. Transcripts corresponding to ADARP1 were found in all the additional RNAs tested with the highest amount present in the testis (like that of the first panel tested). Relative high expression was also observed in skeletal muscle. These data taken with those from the first panel (high in heart) suggest that ADARP1 major role may in the muscle.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polynucleotide comprising a polynucleotide sequence selected from the group consisting of:
   (a) an isolated polynucleotide encoding a polypeptide corresponding to amino acids 1 to 267 of SEQ ID NO:2 including the initiation codon;
   (b) an isolated polynucleotide encoding a polypeptide corresponding to amino acids 2 to 267 of SEQ ID NO:2 minus the initiation codon; and
   (c) an isolated polynucleotide encoding the ADARP1 polypeptide as encoded by the cDNA clone contained in ATCC Deposit No: PTA-2678;
   (d) an isolated polynucleotide which represents the complementary sequence (antisense) of (a), (b), (c).

2. The isolated polynucleotide of claim 1, wherein said polynucleotide is (a).

3. The isolated polynucleotide of claim 2, wherein said polynucleotide comprises nucleotides 201 to 1001 of SEQ ID NO:1.

4. The isolated polynucleotide of claim 1, wherein said polynucleotide is (b).

5. The isolated polynucleotide of claim 4, wherein said polynucleotide comprises nucleotides 204 to 1001 of SEQ ID NO:1.

6. The isolated polynucleotide of claim 1, wherein said polynucleotide is (c).

7. The isolated polynucleotide of claim 1, wherein said polynucleotide is (d).

8. A recombinant vector comprising the isolated polynucleotide of claim 1.

9. A recombinant host cell comprising the vector sequences of claim 8.

10. A method for producing a polypeptide comprising:
    (a) culturing the recombinant host cell of claim 9 under conditions suitable for the expression of said polypeptide; and
    (b) recovering said polypeptide from the recombinant host cell culture.

11. A method for detecting a polynucleotide encoding the ADARP1 polypeptide of SEQ ID NO:2 in a biological sample, comprising the steps of:
    a) hybridizing the polynucleotide according to claim 1 to the nucleic acid material of the biological sample, thereby forming a hybridization complex; and b) detecting the hybridization complex, wherein the presence of the complex correlates with the presence of a polynucleotide encoding the ADARP1 polypeptide in the biological sample, wherein said method only detects the polynucleotide encoding the ADARP1 polypeptide and does not detect the polynucleotide encoding the human ADA polypeptide provided in SEQ ID NO:3 or the murine ADA polypeptide provided in SEQ ID NO:4.

12. The method of claim 11, wherein the nucleic acid material of the biological sample is amplified by the polymerase chain reaction before the hybridizing step.

13. The isolated polynucleotide of claim 1 wherein said polynucleotide further comprises a heterologous nucleic acid sequence.

14. The isolated polynucleotide of claim 13 wherein said heterologous nucleic acid sequence encodes a heterologous polypeptide.

15. The isolated polynucleotide of claim 14 wherein said heterologous polypeptide is the Fc domain of immunoglobulin.

* * * * *

UNITED STATES PATENT AND TRADEMARK OFFICE
CERTIFICATE OF CORRECTION

PATENT NO. : 6,706,513 B2
DATED : March 16, 2004
INVENTOR(S) : Ramanathan et al.

It is certified that error appears in the above-identified patent and that said Letters Patent is hereby corrected as shown below:

<u>Title page,</u>
Item [75], Inventors, please delete inventor "John N. Feder"

Signed and Sealed this

Eighth Day of June, 2004

JON W. DUDAS
*Acting Director of the United States Patent and Trademark Office*

SEQUENCE LISTING

<160> NUMBER OF SEQ ID NOS: 6

<210> SEQ ID NO 1
<211> LENGTH: 1357
<212> TYPE: DNA
<213> ORGANISM: Homo sapiens

<400> SEQUENCE: 1

```
cacgcgtccg cctgtctcaa agaaaaaaa aaaaaaggtg aagctgaacc cagatctaca      60
catacagcta atcttaccaa aatgtgtgga agtaaagcaa tctgaaggaa attcagtacc    120
atacaattta ctgactgaaa tacatcatat tgctcatact aagaataaga gtggagaaga    180
atcatttttt tcctgctaaa atgatagagg cagaagagca acagccttgc aagacagact    240
tctattctga attgccaaaa gtggaacttc atgcccactt gaatggatcc attagttctc    300
ataccatgaa gaaattaata gcccagaagc cagatcttaa aatccacgat cagatgactg    360
tgattgacaa gggaaagaaa agaactttgg aagaatgttt ccagatgttt caaactattc    420
atcagcttac tagtagccct gaagatattc taatggtcac aaaagatgtc ataaaagaat    480
ttgcagatga cggcgtcaag tacctggaac taaggagcac acccagaaga gaaaatgcta    540
ctggaatgac taaaaagact tatgtggaat ctatacttga aggtataaaa cagtccaaac    600
aagaaaactt ggacattgat gttaggtatt tgatagcagt tgacagaaga ggtggcccct    660
tagtagccaa ggagactgta aaacttgccg aggagttctt cctttctact gagggtacag    720
ttcttggcct tgacctcagt ggagacccta ctgtaggaca agcaaaagac ttcttggaac    780
ctctttttaga agctaagaaa gcaggtctga agttagcatt gcatctttca gagattccaa    840
accaaaaaaa agaaacacaa atactcctgg atctgcttcc tgacagaatc gggcatggaa    900
catttctcaa ctccggtgag ggaggatccc tggatctggt ggactttgtg aggcaacatc    960
ggataccact gggtaaggct tggagtttca ggtcttccag atgactctct gtctctcccc   1020
caatccccag gttgcctggg gattacagag aagtactgtt ctaaaagtac gaatgtcatc   1080
tagctattaa aagatggagt gtgtgctttc tgagccttat ttaaaacaga aagctttagc   1140
ttccattaga atataagctc tatgagagca gggcccctgc ttgtcttatt cgttgttaca   1200
ttctccaatg cttggaactc aataagaatt ttttaaagga ataaagggtc atctagaatt   1260
ttaaaatgac tttaacaaaa ttgacatgtg ttatgaaaat atgtaacatt atttaaaaat   1320
taaacatgga aaatcccaag taaaaaaaaa aaaaaaa                             1357
```

<210> SEQ ID NO 2
<211> LENGTH: 267
<212> TYPE: PRT
<213> ORGANISM: Homo sapiens

<400> SEQUENCE: 2

```
Met Ile Glu Ala Glu Glu Gln Gln Pro Cys Lys Thr Asp Phe Tyr Ser
  1               5                  10                  15

Glu Leu Pro Lys Val Glu Leu His Ala His Leu Asn Gly Ser Ile Ser
             20                  25                  30

Ser His Thr Met Lys Lys Leu Ile Ala Gln Lys Pro Asp Leu Lys Ile
         35                  40                  45

His Asp Gln Met Thr Val Ile Asp Lys Gly Lys Lys Arg Thr Leu Glu
     50                  55                  60

Glu Cys Phe Gln Met Phe Gln Thr Ile His Gln Leu Thr Ser Ser Pro
```

```
            65                  70                  75                  80
Glu Asp Ile Leu Met Val Thr Lys Asp Val Ile Lys Glu Phe Ala Asp
                        85                  90                  95

Asp Gly Val Lys Tyr Leu Glu Leu Arg Ser Thr Pro Arg Arg Glu Asn
            100                 105                 110

Ala Thr Gly Met Thr Lys Lys Thr Tyr Val Glu Ser Ile Leu Glu Gly
            115                 120                 125

Ile Lys Gln Ser Lys Gln Glu Asn Leu Asp Ile Asp Val Arg Tyr Leu
        130                 135                 140

Ile Ala Val Asp Arg Arg Gly Gly Pro Leu Val Ala Lys Glu Thr Val
145                 150                 155                 160

Lys Leu Ala Glu Glu Phe Phe Leu Ser Thr Glu Gly Thr Val Leu Gly
                    165                 170                 175

Leu Asp Leu Ser Gly Asp Pro Thr Val Gly Gln Ala Lys Asp Phe Leu
                180                 185                 190

Glu Pro Leu Leu Glu Ala Lys Lys Ala Gly Leu Lys Leu Ala Leu His
            195                 200                 205

Leu Ser Glu Ile Pro Asn Gln Lys Lys Glu Thr Gln Ile Leu Leu Asp
        210                 215                 220

Leu Leu Pro Asp Arg Ile Gly His Gly Thr Phe Leu Asn Ser Gly Glu
225                 230                 235                 240

Gly Gly Ser Leu Asp Leu Val Asp Phe Val Arg Gln His Arg Ile Pro
                245                 250                 255

Leu Gly Lys Ala Trp Ser Phe Arg Ser Ser Arg
            260                 265

<210> SEQ ID NO 3
<211> LENGTH: 363
<212> TYPE: PRT
<213> ORGANISM: Homo sapiens

<400> SEQUENCE: 3

Met Ala Gln Thr Pro Ala Phe Asp Lys Pro Lys Val Glu Leu His Val
  1               5                  10                  15

His Leu Asp Gly Ser Ile Lys Pro Glu Thr Ile Leu Tyr Tyr Gly Arg
                20                  25                  30

Arg Arg Gly Ile Ala Leu Pro Ala Asn Thr Ala Glu Gly Leu Leu Asn
            35                  40                  45

Val Ile Gly Met Asp Lys Pro Leu Thr Leu Pro Asp Phe Leu Ala Lys
        50                  55                  60

Phe Asp Tyr Tyr Met Pro Ala Ile Ala Gly Cys Arg Glu Ala Ile Lys
65                  70                  75                  80

Arg Ile Ala Tyr Glu Phe Val Glu Met Lys Ala Lys Glu Gly Val Val
                85                  90                  95

Tyr Val Glu Val Arg Tyr Ser Pro His Leu Leu Ala Asn Ser Lys Val
            100                 105                 110

Glu Pro Ile Pro Trp Asn Gln Ala Glu Gly Asp Leu Thr Pro Asp Glu
        115                 120                 125

Val Val Ala Leu Val Gly Gln Gly Leu Gln Glu Gly Glu Arg Asp Phe
    130                 135                 140

Gly Val Lys Ala Arg Ser Ile Leu Cys Cys Met Arg His Gln Pro Asn
145                 150                 155                 160

Trp Ser Pro Lys Val Val Glu Leu Cys Lys Asn Tyr Gln Gln Gln Thr
                165                 170                 175
```

```
Val Val Ala Ile Asp Leu Ala Gly Asp Glu Thr Ile Pro Gly Ser Ser
            180                 185                 190

Leu Leu Pro Gly His Val Gln Ala Tyr Gln Glu Ala Val Lys Ser Gly
        195                 200                 205

Ile His Arg Thr Val His Ala Gly Glu Val Gly Ser Ala Glu Val Val
    210                 215                 220

Lys Glu Ala Val Asp Ile Leu Lys Thr Glu Arg Leu Gly His Gly Tyr
225                 230                 235                 240

His Thr Leu Glu Asp Gln Ala Leu Tyr Asn Arg Leu Arg Gln Glu Asn
                245                 250                 255

Met His Phe Glu Ile Cys Pro Trp Ser Ser Tyr Leu Thr Gly Ala Trp
            260                 265                 270

Lys Pro Asp Thr Glu His Ala Val Ile Arg Leu Lys Asn Asp Gln Ala
        275                 280                 285

Asn Tyr Ser Leu Asn Thr Asp Pro Leu Ile Phe Lys Ser Thr Leu
    290                 295                 300

Asp Thr Asp Tyr Gln Met Thr Lys Arg Asp Met Gly Phe Thr Glu Glu
305                 310                 315                 320

Glu Phe Lys Arg Leu Asn Ile Asn Ala Ala Lys Ser Ser Phe Leu Pro
                325                 330                 335

Glu Asp Glu Lys Arg Glu Leu Leu Asp Leu Leu Tyr Lys Ala Tyr Gly
            340                 345                 350

Met Pro Pro Ser Ala Ser Ala Gly Gln Asn Leu
        355                 360

<210> SEQ ID NO 4
<211> LENGTH: 352
<212> TYPE: PRT
<213> ORGANISM: Mus musculus

<400> SEQUENCE: 4

Met Ala Gln Thr Pro Ala Phe Asn Lys Pro Lys Val Glu Leu His Val
1               5                   10                  15

His Leu Asp Gly Ala Ile Lys Pro Glu Thr Ile Leu Tyr Phe Gly Lys
            20                  25                  30

Lys Arg Gly Ile Ala Leu Pro Ala Asp Thr Val Glu Glu Leu Arg Asn
        35                  40                  45

Ile Ile Gly Met Asp Lys Pro Leu Ser Leu Pro Gly Phe Leu Ala Lys
    50                  55                  60

Phe Asp Tyr Tyr Met Pro Val Ile Ala Gly Cys Arg Glu Ala Ile Lys
65                  70                  75                  80

Arg Ile Ala Tyr Glu Phe Val Glu Met Lys Ala Lys Glu Gly Val Val
                85                  90                  95

Tyr Val Glu Val Arg Tyr Ser Pro His Leu Leu Ala Asn Ser Lys Val
            100                 105                 110

Asp Pro Met Pro Trp Asn Gln Thr Glu Gly Asp Val Thr Pro Asp Asp
        115                 120                 125

Val Val Asp Leu Val Asn Gln Gly Leu Gln Glu Gly Glu Gln Ala Phe
    130                 135                 140

Gly Ile Lys Val Arg Ser Ile Leu Cys Cys Met Arg His Gln Pro Ser
145                 150                 155                 160

Trp Ser Leu Glu Val Leu Glu Leu Cys Lys Lys Tyr Asn Gln Lys Thr
                165                 170                 175

Val Val Ala Met Asp Leu Ala Gly Asp Glu Thr Ile Glu Gly Ser Ser
            180                 185                 190
```

```
Leu Phe Pro Gly His Val Glu Ala Tyr Glu Gly Ala Val Lys Asn Gly
        195                 200                 205

Ile His Arg Thr Val His Ala Gly Glu Val Gly Ser Pro Glu Val Val
        210                 215                 220

Arg Glu Ala Val Asp Ile Leu Lys Thr Glu Arg Val Gly His Gly Tyr
225                 230                 235                 240

His Thr Ile Glu Asp Glu Ala Leu Tyr Asn Arg Leu Leu Lys Glu Asn
            245                 250                 255

Met His Phe Glu Val Cys Pro Trp Ser Ser Tyr Leu Thr Gly Ala Trp
            260                 265                 270

Asp Pro Lys Thr Thr His Ala Val Val Arg Phe Lys Asn Asp Lys Ala
            275                 280                 285

Asn Tyr Ser Leu Asn Thr Asp Asp Pro Leu Ile Phe Lys Ser Thr Leu
        290                 295                 300

Asp Thr Asp Tyr Gln Met Thr Lys Lys Asp Met Gly Phe Thr Glu Glu
305                 310                 315                 320

Glu Phe Lys Arg Leu Asn Ile Asn Ala Ala Lys Ser Ser Phe Leu Pro
                325                 330                 335

Glu Glu Glu Lys Lys Glu Leu Leu Glu Arg Leu Tyr Arg Glu Tyr Gln
            340                 345                 350
```

<210> SEQ ID NO 5
<211> LENGTH: 22
<212> TYPE: DNA
<213> ORGANISM: Homo sapiens

<400> SEQUENCE: 5
acgaggagca atctgaagga aa                                        22

<210> SEQ ID NO 6
<211> LENGTH: 26
<212> TYPE: DNA
<213> ORGANISM: Homo sapiens

<400> SEQUENCE: 6
tcatggtatg agaactaatg gatcca                                    26